United States Patent [19]

Eischen, Sr.

[11] Patent Number: 4,805,601

[45] Date of Patent: Feb. 21, 1989

[54] DEVICE FOR LOWER LIMB EXTREMITY HAVING WEIGHT-RESPONSE PRESSURE CHAMBERS

[76] Inventor: Clement G. Eischen, Sr., 601 NE. 167th Pl., Portland, Oreg. 97230

[21] Appl. No.: 24,863

[22] Filed: Mar. 12, 1987

Related U.S. Application Data

[63] Continuation of Ser. No. 712,180, Mar. 15, 1985, abandoned.

[51] Int. Cl.[4] .......... A61F 5/00; A61H 9/00

[52] U.S. Cl. .......... 128/64; 128/80 H

[58] Field of Search .......... 128/80 H, 80 D, 582, 128/24 R, D20, 64

[56] References Cited

U.S. PATENT DOCUMENTS

| | | | |
|---|---|---|---|
| 1,257,086 | 2/1918 | Marcellus | 36/88 |
| 2,531,074 | 11/1950 | Miller | 128/D20 |
| 2,694,395 | 11/1954 | Brown | 128/DIG. 20 |
| 3,083,708 | 4/1963 | Gottfried | 128/64 |
| 3,403,673 | 10/1968 | MacLeod | 128/64 |
| 3,469,576 | 9/1969 | Smith et al. | 128/595 |
| 3,548,809 | 12/1970 | Conti | 128/64 |
| 3,824,992 | 7/1974 | Nicholson et al. | 128/64 |
| 3,888,242 | 6/1975 | Harris et al. | 128/64 |
| 4,067,063 | 1/1978 | Ettinger | 2/2 |
| 4,128,951 | 12/1978 | Tansill | 36/44 |
| 4,166,460 | 9/1979 | Applegate | 128/80 H |
| 4,227,320 | 10/1980 | Borgeas | 128/80 D |
| 4,263,905 | 4/1981 | Couch, Jr. | 128/149 |
| 4,266,298 | 5/1981 | Graziano | 128/89 |
| 4,370,975 | 2/1983 | Wright | 128/64 |
| 4,502,470 | 3/1985 | Kiser et al. | 128/582 |

FOREIGN PATENT DOCUMENTS

| | | | |
|---|---|---|---|
| 960537 | 1/1975 | Canada | 128/D20 |
| 0039629 | 4/1981 | European Pat. Off. | 128/582 |
| 2737734 | 12/1978 | Fed. Rep. of Germany | 128/80 R |
| 260822 | 10/1970 | U.S.S.R. | 128/64 |
| 197710 | 10/1977 | U.S.S.R. | 128/64 |

*Primary Examiner*—Edgar S. Burr
*Assistant Examiner*—Tonya Lamb
*Attorney, Agent, or Firm*—Kolisch, Hartwell & Dickinson

[57] ABSTRACT

Therapeutic device for wearing by an individual on a lower extremity to facilitate rehabilitation of a injured foot, ankle and/or lower leg area by promoting venous blood flow in the injured area includes a first pressurized chamber configured for imparting fluid pressure to the injured area and a weight-responsive second chamber coactable with the first pressurized chamber for providing recurrent compression to the injured area by varying the fluid pressure imparted by the first pressurized chamber. The first pressurized chamber is dimensioned to surround substantially the injured area, and the weight-responsive chamber communicates fluidwise with the first chamber and is resiliently deformable volumewise upon impaction by a force to displace fluid alternately into and from the first pressurized chamber.

6 Claims, 2 Drawing Sheets

DEVICE FOR LOWER LIMB EXTREMITY HAVING WEIGHT-RESPONSE PRESSURE CHAMBERS

This application is a continuation of application Ser. No. 06/712,180 filed Mar. 15, 1985, now abandoned.

BACKGROUND AND SUMMARY OF THE INVENTION

The present invention relates to rehabilitation of injuries, and particularly to a novel therapeutic appliance or device for wearing by an individual to promote healing of an injured foot, ankle or lower leg area. The therapeutic device of the present invention may be comfortably worn as a shoe or boot, and provides recurrent compression or "massaging" of the injured area by variable fluid or air pressure.

Injuries to the foot, ankle and lower leg are very common, and can result from industrial accidents, day-to-day activities and are increasingly prevalent because of widespread participation in athletics. Typical injuries to the lower leg include contusions which may vary from a mild bruise to serious injuries. Rupture of the gastrocnemius muscle or "tennis leg" is a condition resulting from a tear of the junction of one of the heads of the gastrocnemius muscle. Treatment generally constitutes applying a cold, wet elastic bandage for compression. Ice is then applied on top of one or two layers of this bandage and held firmly in place with further wraps, the leg being elevated and the foot held in generally plantar flexion. The individual should then walk only in a non-weight-bearing manner with crutches.

Injuries to the ankle are very common, and generally include sprains, although fractures may sometimes occur. The bulk of all ankle sprains are inversion injuries, occurring, in athletics, when an athlete runs straight ahead or cuts and the foot suddenly turns into plantar flexion and inversion. Sharp pain results from the ligaments being sprained and is accompanied by swelling and lack of flexibility. Concerning treatment, general guidelines include having the individual placed in a non-weight-bearing position and application of a cold wrap to support the ankle, after which an ice bag is placed on the bandage to give compression with wrapping being continued. If the injury appears to be relatively severe, the leg should be elevated and x-rays taken to determine if fracture has occurred. If there is no fracture, then the rehabilitation process generally involves a program over several days involving ice, compression through bandages, and elevation, followed eventually by use of crutches so that weight-bearing can be increased gradually. Ice and ice massage may be applied to the injured area frequently prior to the individual walking with crutches.

With respect to foot injuries, sprains and fractures may also occur in that area. Treatment of sprains in the foot is similar to that for ankles, and in the case of fractures to the ankle or foot, a cast must be worn and after healing of the fracture, swelling, stiffness and pain may still result. Other injuries to the lower leg/foot area may include sprains and ruptures to the achilles tendon.

In any case, it is the rehabilitation of a sprained ankle or foot, or damage to a torn gastrocnemius muscle, resulting in swelling, which the present invention is particularly noteworthy in treating. The present invention involves a therapeutic device for facilitating rehabilitation of lower leg, ankle and foot injuries, including the sprains and tears as outlined above, and is also used as a post-operative device, i.e., after surgery or after a cast has been removed to reduce swelling and diminish pain.

The healing process is greatly facilitated if the injured area can be massaged or compressed, i.e., if the venous blood flow to the traumatized area can be promoted. Venous blood flow helps the healing process by taking away waste products and bringing in nutrients which supply the cells. Whirlpools are not as efficient as direct massaging or compression, and the present invention provides this action.

It is a general object of the present invention to provide a simple therapeutic appliance or device, which can be worn by an individual to facilitate healing of a sprain, or to provide post-operative rehabilitation of an injured or traumatized foot, ankle or lower leg, by promoting venous blood flow in the injured area. The therapeutic device includes a flexible and inflatable first pressurized means, formed as a fluid-receiving first chamber dimensioned to surround substantially the injured area for imparting fluid pressure to that area. The therapeutic device also incorporates a weight-responsive means coactable with the first pressurized means for providing recurrent compression to the injured area by varying the fluid pressure imparted by the first chamber.

It is another object of the present invention to provide a therapeutic device, as described above, in which the weight-responsive means is defined by a fluid-receiving second chamber communicating fluidwise with the first chamber. The second chamber is resiliently deformable to displace fluid alternately into and from the first chamber by a motive force generated when the individual walks.

Still another object of the present invention is to provide a therapeutic device, as described above, in which the second chamber is secured to the first chamber and is positionable therebeneath and in contact with the bottom of an individual's foot. Thus, when the individual walks, his/her weight will compress the second chamber to displace fluid therefrom into the first chamber, thereby to increase the pressure within the first chamber and on the injured area. When the individual lifts his/her foot, i.e., adopts a non-weight-bearing stance, the second chamber expands to draw fluid from the first chamber, thereby to decrease the pressure within the first chamber and correspondingly on the injured area. The net effect, during walking by an individual, is recurrent compression to the injured area which promotes venous blood flow in that area, and consequently promotes healing.

These and additional objects and advantages of the present invention will be more readily understood after a consideration of the drawings and the detailed description of the preferred embodiment.

DETAILED DESCRIPTION OF THE PREFERRED EMBODIMENT

As mentioned at the outset, an object of the present invention is to provide a therapeutic device which may be worn by an individual to provide rehabilitation of an injured foot, ankle or lower leg area by promoting venous blood flow in the injured area. To accomplish that result, the present invention provides an appliance or device which includes a first pressurized means for imparting fluid pressure to the injured area and a weight-responsive means coactable with the first pressurized means for varying the fluid pressure imparted by the first pressurized means to the injured area. By varying the pressure applied to the injured area, recurrent compression results, and venous blood flow in the injured area is promoted which aids in the rehabilitation process.

Figure 1:
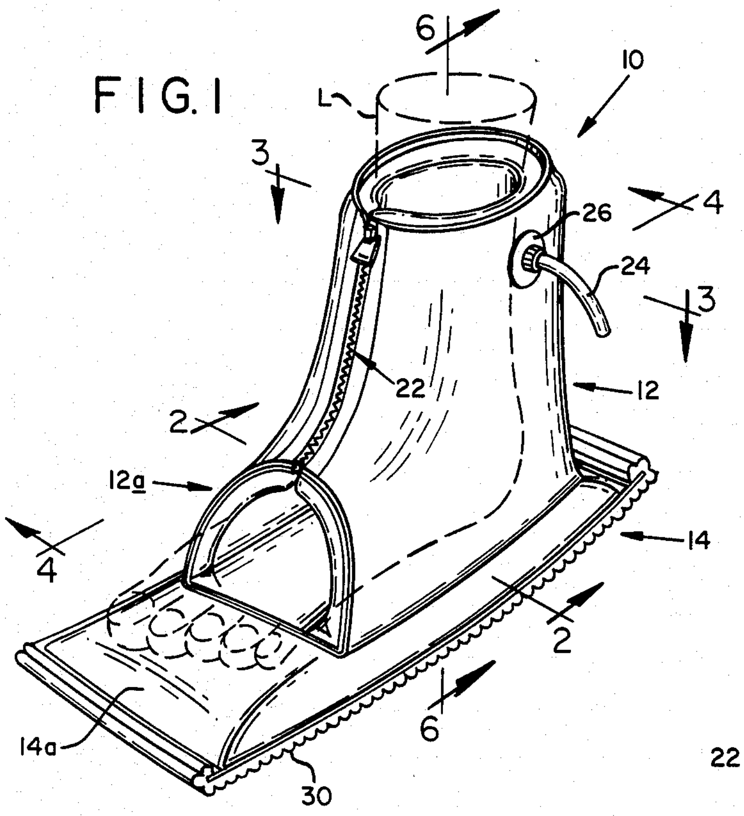
FIG. 1 is a perspective view of the therapeutic device of the present invention illustrating it positioned for wearing around an individual's foot, ankle and a portion of the lower leg, shown in dashed lines.

As shown in FIG. 1, a therapeutic device in accordance with the present invention, generally indicated at 10, includes a first pressurized means 12, configured for wearing around the lower leg of an individual, indicated at L, so as to surround substantially the ankle region and the foot. Therapeutic device 10 includes a weight-responsive means 14 which is coactable, in a manner to be described, with first pressurized means 12 for providing recurrent compression to an injured area, such as an injury to the foot, ankle or lower leg.

Figure 2:
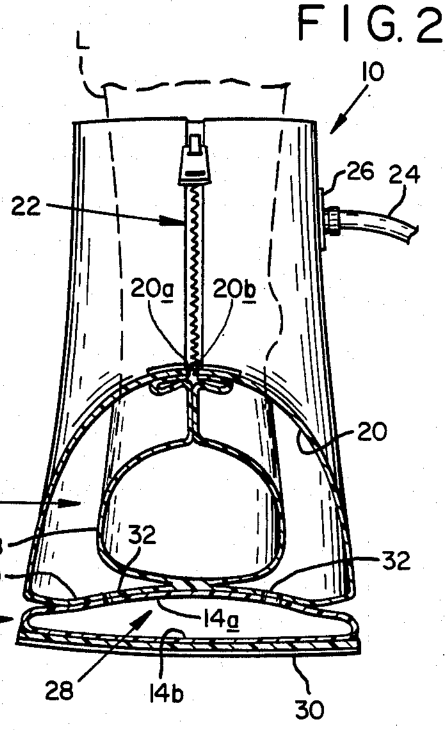
FIG. 2 is a cross-sectional view taken along lines 2—2 of FIG. 1 and shows construction of the first pressurized means or first chamber and the weight-responsive means or second chamber.

First pressurized means 12 is formed of flexible material, for comfortable wearing by an individual on a lower extremity, and may be thought of as an inflatable bag, one which is resiliently deformable volumewise. First pressurized means 12 (see FIGS. 2 and 3 also) defines a first chamber, generally indicated at 16, which is formed between a pair of panels, an internal panel or wall indicated at 18, engageable with the foot, ankle and/or lower leg area, and an external panel or wall indicated at 20. The internal and external walls are formed of flexible, plastic material and are joined along their edges to form a cavity therebetween, which cavity becomes first chamber 16, when pressurized in a manner to be hereinafter described. The panels are arranged so that they receive the foot, ankle and lower leg area of an individual, such as shown in FIG. 2. Marginal edges **20*a*, 20*b* may be drawn together by a zipper 22** which is provided for affixing the first pressurized means to the foot. The zipper may of course be slided downwardly to release the marginal edges so the foot may be inserted initially or withdrawn.

Figure 3:
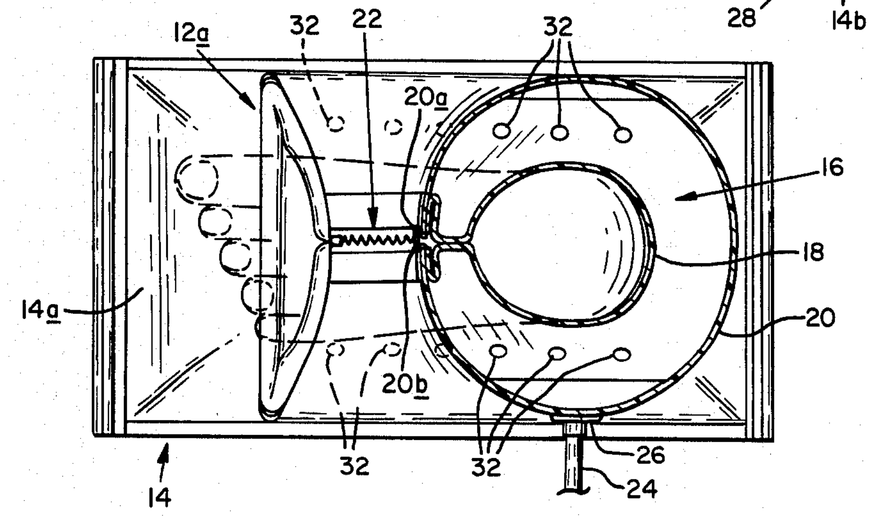
FIG. 3 is a top plan view of FIG. 1.

It is also to be noted, as shown in FIGS. 1-3, that a valve stem, shown at 24, is secured to a fitting 26 provided in external wall 20. The valve stem is provided so that an individual may inflate first chamber 16 with air, via lung power, to inflate the area between the internal and external walls. The valve stem may be suitably capped or tied off.

As shown in FIGS. 1 and 3, the front of first pressurized means 12, generally indicated at **12*a*, is open so that when zipper 22 is not fastened, an individual's foot and lower leg may be slipped into the interior of internal wall 18 so that the toes extend outwardly therefrom. The zipper, upon being drawn upwardly for fastening, closes first pressurized means 10 around the foot, ankle and lower leg so that when air is introduced through valve stem 24**, the aforementioned inflation occurs.

Now, referring to an important feature of the present invention, attention is directed to weight-responsive means 14 as shown in FIGS. 1 and 2. The weight-responsive means is formed also of flexible, plastic material, and may also be thought of as an inflatable bag or envelope defining another, or a second, fluid-receiving chamber 28 which includes a top wall **14*a* secured, as by heat sealing or welding, to a portion of a bottom wall of external wall 20. The second chamber is also resiliently deformable volumewise, particularly upon impaction by a compressive force. A bottom wall 14*b* of weight-responsive means 14 is secured to impact-absorbing material, such as a ribbed, elastomeric tread or sole indicated at 30**.

Second chamber 28 communicates fluidwise with first chamber 16 by a fluid transfer means, which may be take the form of openings or apertures such as indicated at 32. The apertures extend through top wall **14*a* into associated apertures in the bottom portion of external wall 20 as shown in FIGS. 2 and 3. Thus, the second chamber is in fluid communication with first chamber 16**, and that fluid communication, permitting fluid transfer between the two chambers, enables recurrent compression to be imparted to the injured area in a manner now to be described.

Figure 4:
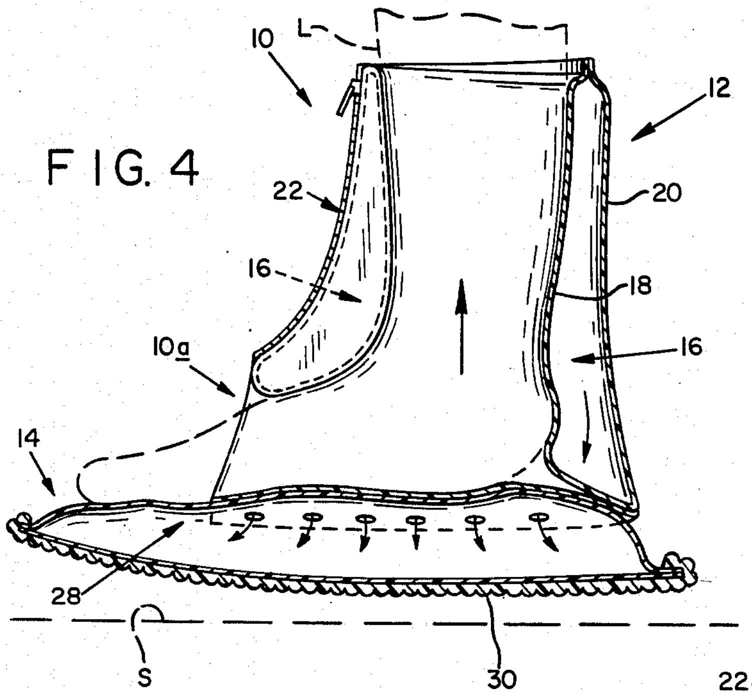
FIG. 4 is a side cross-sectional view taken along lines 4—4 of FIG. 1 and illustrates expansion of the second chamber when the individual lifts his/her foot during walking.

Initially, it is presumed that first and second chambers 16, 28, respectively, are noninflated, and that zipper 22 is open so that an individual may slide his/her foot into the envelope or receiving pocket created within the interior surface of internal wall 18, so that the foot is positioned to extend, as shown in FIG. 3, with the toes overlying top wall **14*a* of weight-responsive means 14. The zipper then is drawn upwardly so that internal wall 18 closes and fits loosely around the foot, ankle area and lower leg. Next, by the individual blowing into valve stem 24, air is introduced into first chamber 16 so as to inflate the first chamber to dispose air pressure outwardly against external wall 20 and inwardly against internal wall 18, which results in air pressure being imparted to the injured area, which is taken to be that area surrounded by the first chamber. As shown in FIG. 4, and assuming that no weight has been brought to bear by the individual against weight-responsive means 14, air introduced through first chamber 16 is channeled or transferred through apertures 32 to inflate also second chamber 28**.

Figure 5:
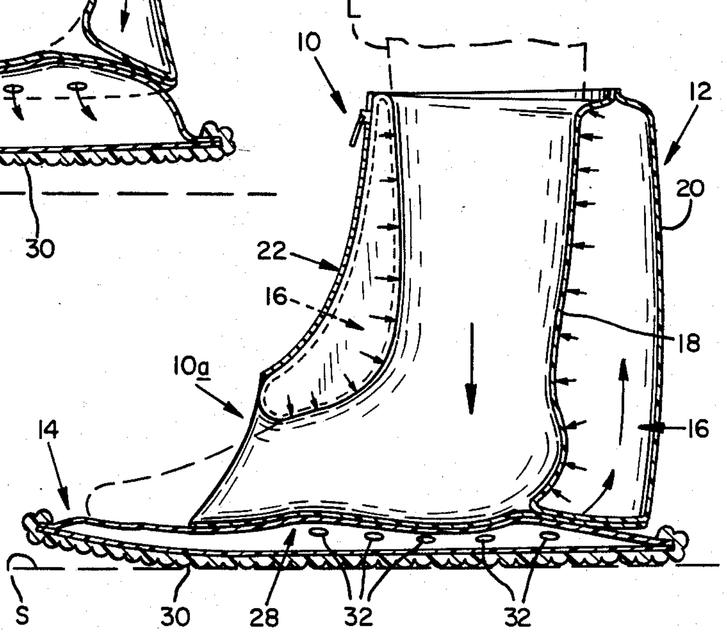
FIG. 5 is a view similar to that shown in FIG. 4, and illustrates increased pressurization within the first chamber when the individual places weight upon the second chamber.
Figure 6:
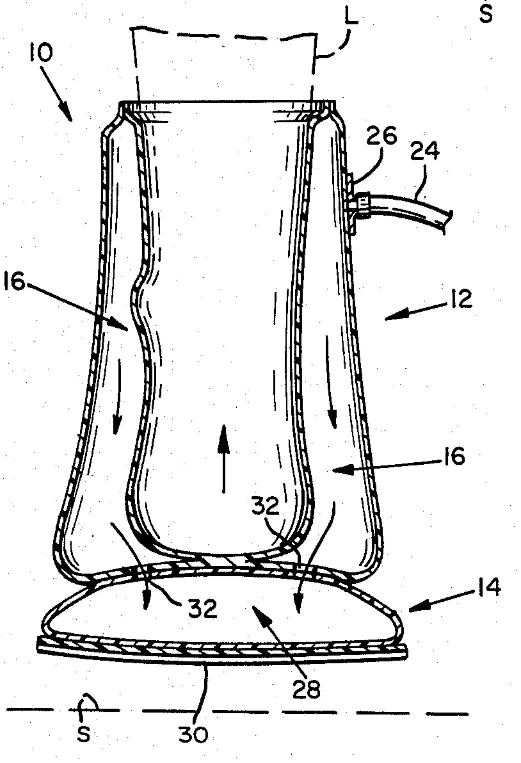
FIG. 6 is a view taken along lines 6—6 of FIG. 1 and illustrates substantially equal pressurization of the first and second chambers when the individual's weight is not placed on the second chamber.
Figure 7:
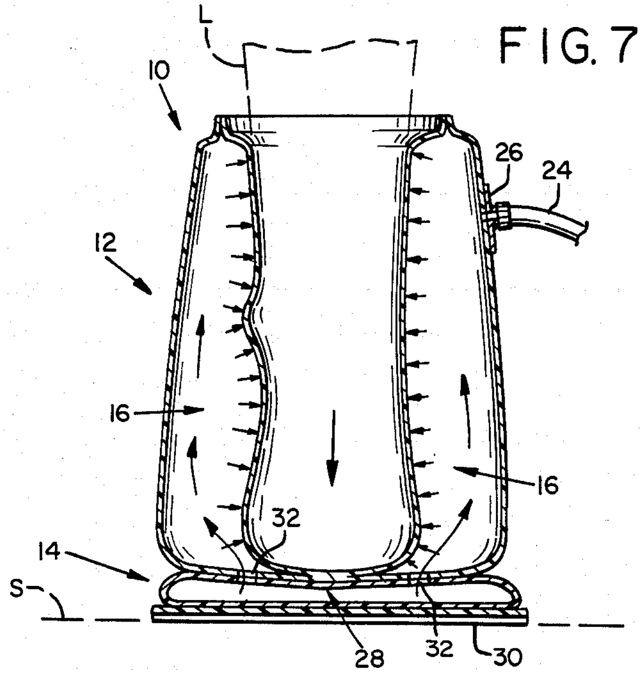
FIG. 7 is a view similar to FIG. 6, except that the individual's weight has been brought to bear on the second chamber.

After valve stem 24 has been suitably tied or capped off, and assuming still that no force or weight has been applied to weight-responsive means 14, the pressure within the first and second chambers will be substantially the same, i.e., a state of pressure equilibrium will have been attained. However, if an individual bears a portion of his/her weight on weight-responsive means 14, as by engaging sole 30 against a surface S, pressure will become nonequalized, i.e., the second chamber being deformable will be compressed to displace air into first chamber 16 to increase the pressure applied to the foot, ankle and lower leg area as shown in FIGS. 5 and 7. As long as impaction of a force continues on the weight-responsive means, so that second chamber 28 is deformed, there will be a fluid pressure increase in first chamber 16. As the individual relaxes the pressure exerted by his/her foot on the weight-responsive means, as during the stride phase in walking, second chamber 28 deforms or expands, as shown in FIG. 4 again (also FIG. 6), so that pressure equalizes in the first and second chambers, thereby diminishing the pressure in the first chamber.

The recurrent compression to the injured area, caused by varying the air pressure imparted by the first pressurized means, "massages" the injured area and thereby facilitates rehabilitation and healing by promoting venous blood flow. The weight-responsive means may be thought of as a pump, actuated by the individual's weight when he/she walks or otherwise alternately compresses and expands the second chamber volume-wise to displace fluid alternately into and withdraw it from the first chamber.

While the present invention has been shown with respect to a therapeutic device covering a portion of the lower leg, it should be appreciated that by dimensioning the appliance so that it extends up over the calf, a first chamber could be provided for imparting the massaging or recurrent compression, via actuation of the second chamber, to a calf area which has been traumatized and is subject to edema or swelling. In addition, while the toes have been shown extending through an opening 10*a* in the device, it could be easily constructed so that the toes were covered. In addition, the concept of a first chamber relative to another body part, such as the knee, could also be provided and connected to a second chamber positioned beneath and in contact with an individual's foot so that upon walking, the individual's weight would compress the second chamber to displace fluid therefrom into the first chamber, which in this case being around the knee, would provide compression to that area if desired.

There are several very distinct and important advantages which result from the construction of the present invention. First of all, a very simple and trouble-free appliance has been provided. The device enables an individual to become at least partially ambulatory, i.e., a person suffering from a bad sprain or recovering in a post-operative condition may facilitate rehabilitation of an injured area, by walking on crutches so that the recurrent compression using the present invention may be employed. The recurrent compression or massaging, which increases the venous blood flow, greatly helps the healing process because waste products are removed and new blood is distributed to the cells for providing nutrition.

A specific advantage of the present invention is that the amount of compression to be applied, as during walking, is solely dependent upon the individual. Stated another way, an individual may selectively gauge and provide the desired amount of weight applied to the second chamber to increase/decrease the fluid pressure within the first chamber. If it is too painful for the individual to bear most of his/her weight downwardly, variations can be selected by the individual.

While the present invention has been shown and described with reference to the foregoing preferred embodiment, it will be appreciated by those skilled in the art that other changes in form and detail may be made therein without departing from the spirit and scope of the invention as defined in the appended claims.

It is claimed and desired to secure by Letters Patent:

1. A therapeutic device adapted to be worn by an individual on a lower limb extremity to promote rehabilitation of the extremity by promoting venus blood flow comprising:

a first flexibly walled inflatable envelope structure having a first internal chamber for receiving fluid under pressure, the envelope structure including said first chamber being dimensioned substantially to surround the lower limb extremity, wherein said first envelope structure comprises opposed internal and external panels each having a first and an opposite edge, said first edges being joined to each other to form one marginal edge of the envelope structure and said opposite edges being joined to each other to form an opposite marginal edge of the envelope structure, said envelope structure when positioned on the lower limb extremity forming a sleeve encircling the ankle and the internal and external panels then defining said first chamber which similarly encircles the ankle, means for securing the envelope structure, said means completing the substantially surrounding envelopment of the lower limb extremity by said envelope structure, wherein said securing means comprises means for detachably securing said one and said opposite marginal edges of the envelope structure together, another flexibly walled envelope structure having another internal chamber for receiving fluid under pressure, said other envelope structure including said other chamber being dimensioned to underlie the foot of the lower limb extremity in a region extending between the opposite lateral sides of the foot, and fluid transfer means interconnecting said first and said other chamber, compression of said other envelope structure under foot pressure operating to transfer fluid under pressure from said other to said first chamber to produce isostatic compression of said lower limb extremity, and decompression of said other envelope structure in the absence of foot pressure operating to return the pressure of the fluid in said first and said other chamber to equilibrium.

2. The therapeutic device of claim 1, wherein said other flexibly walled envelope structure comprises opposed top and bottom panels defining therebetween said other chamber, said top and bottom panels and said chamber having an extent whereby such extend under the entire foot with the device in an operative position.

3. A therapeutic device for wearing by a user on a lower limb extremity to promote rehabilitation of such extremity by promoting venous blood flow in the ankle area comprising:

a first flexibly walled inflatable envelope structure having an internal chamber for receiving fluid under pressure, said structure comprising internal and external panels and said panels each having a first and an opposite edge, said first edges being joined to one another to form one marginal edge of the structure and said opposite edges being joined to one another to form an opposite marginal edge of the envelope structure, said envelope structure having a construction whereby, with the device in operative position, the structure forms a snugly fitting sleeve encircling the ankle of the user with the internal chamber of the structure similarly encircling the ankle, said marginal edges then lying adjacent each other and extending along the length of the ankle, securing means for securing said marginal edges of said envelope structure to each other to integrate the sleeve, another flexibly walled envelope structure having another internal chamber for receiving fluid under pressure, said other envelope structure comprising a top and a bottom panel defining therebetween said other chamber and, with the device in operative position, having an extend which extends under the foot completely from end to end and from side-to-side, means securing said other envelope structure to the first envelope structure, and fluid transfer means interconnecting the internal chamber of the first envelope structure and said other chamber, foot pressure exerted against said other envelope structure operating to transfer fluid from said other to said first mentioned chamber to produce isostatic pressure application in a region encircling the ankle of the user, said foot pressure not exerted operating to return the pressure of the fluid in said first and said other chamber to equilibrium.

4. The therapeutic device of claim 3, further including inflating-deflating means for pressurizing said first and said other chamber, wherein a valve selectively operates to allow introduction of air by blowing into said first and said other chambers and expulsion of air from said first and said other chambers.

5. The therapeutic device of claim 4, wherein said other flexibly walled envelope structure exposes the front portion of the foot not in contact with said first flexibly walled envelope structure, thereby allowing the user freedom of access and movement.

6. The therapeutic device of claim 3, wherein said other flexibly walled envelope structure exposes the front portion of the foot not in contact with said first flexibly walled envelope structure, thereby allowing the user freedom of access and movement.

* * * * *